(12) United States Patent
Prevost et al.

(10) Patent No.: US 8,257,951 B2
(45) Date of Patent: *Sep. 4, 2012

(54) ETHANOL PRODUCTION PROCESS

(75) Inventors: John E. Prevost, Slaughter, LA (US); Neal A. Hammond, Cameron Park, CA (US)

(73) Assignee: Little Sioux Corn Processors, LLC., Marcus, IA (US)

( * ) Notice: Subject to any disclaimer, the term of this patent is extended or adjusted under 35 U.S.C. 154(b) by 369 days.

This patent is subject to a terminal disclaimer.

(21) Appl. No.: 10/281,490

(22) Filed: Oct. 28, 2002

(65) Prior Publication Data
US 2006/0194296 A1 Aug. 31, 2006

(51) Int. Cl.
*C12P 7/06* (2006.01)

(52) U.S. Cl. .......... 435/161; 435/67; 435/71.1; 435/804

(58) Field of Classification Search .................... None
See application file for complete search history.

(56) References Cited

U.S. PATENT DOCUMENTS

| | | | | |
|---|---|---|---|---|
| 2,446,913 A | * | 8/1948 | Erlich | 426/271 |
| 2,543,897 A | * | 3/1951 | De Becze et al. | 435/66 |
| 3,721,568 A | * | 3/1973 | Wilson | 426/452 |
| 5,316,782 A | * | 5/1994 | Zimlich, III | 426/624 |
| 5,503,750 A | * | 4/1996 | Russo et al. | 210/641 |

FOREIGN PATENT DOCUMENTS
WO WO 9422009 * 9/1994

OTHER PUBLICATIONS

"The Phytochemistry of Herbs" ( http://www.herbalchem.net/Carotenoids_Introductory.htm).*
"The Phytochemistry of Herbs" ( http://www.herbalchem.net/Carotenoids_Introductory.htm) (Nov. 1, 2005).*
Wu et al., Recovery of Protein-Rich Byproducts from Sweet Potato Stillage following Alcohol Distillation. J. of Agricultural and Food Chemistry. 1987, vol. 35, No. 3, pp. 321-325.*
Zuohua et al., Chapter 7, pp. 88-99 "http://www.eseap.cipotato.org/MF-ESEAP/Publications/PH-China-2004/07-Chapter-7.pdF".*

* cited by examiner

*Primary Examiner* — Irene Marx
(74) *Attorney, Agent, or Firm* — Camille L. Urban

(57) ABSTRACT

An improved ethanol production process providing novel stillage treatment is disclosed wherein the stillage is separated into four value added product streams that are subjected to drying conditions reducing or eliminating volatization of any VOC's in the product streams.

10 Claims, 4 Drawing Sheets

ETHANOL PRODUCTION PROCESS

BACKGROUND OF THE INVENTION

1. Field of the Invention

This invention relates in general to ethanol production processes, and more particularly to ethanol production processes having enhanced value products produced from the whole stillage and/or reduced volatile organic compounds (VOC) emissions from the process.

2. Prior Art

In a conventional ethanol production process utilizing corn as the starch containing feedstock, the corn is ground to produce a milled corn. This is typically achieved by the use of a hammer mill or other similar conventional milling equipment. Water and enzymes are added to the milled corn and heated to form a liquefied mash. The liquefied mash is then mixed in a fermentation vessel with water, yeast and selected minerals and nutrients to enhance the fermentation of the mash. The fermented product, commonly referred to as the "beer", is then distilled to produce an ethanol rich stream (about 95% ethanol and 5% water by weight) and a whole stillage. The whole stillage comprises water, as well as the solids resulting from the fermentation. It is typical to centrifuge the whole stillage to remove a substantial portion of the water to form a wet distillers grain. The wet distillers grain includes most of the protein containing solids that is found in the whole stillage. The removed water containing nutrients and other solids generally known as the thin stillage is sent to an evaporator to remove a substantial portion of the water. The remaining nutrients and solids called the syrup are then combined with the wet distillers grain. The combined syrup and wet distillers grain is sent to a dryer to produce a dry protein containing animal feed called distiller dried grain solubles (DDGS).

These prior art ethanol processes have several significant problems. One problem is the energy costs to remove the water from the whole stillage to produce a low economic value DDGS. A second problem is the environmentally unacceptable amount of VOC's, air toxics, and combustion pollutants, such as CO, $NO_x$, and particulate matter, released into the atmosphere during the drying process. To achieve an acceptable VOC, air toxics, and combustion pollutants release amount requires large capital investments in thermal oxidizers and other equipment to capture the VOC, air toxics, and combustion pollutants released during the drying process, as well as expensive annual equipment maintenance. These problems have hampered the commercial success of ethanol production processes that have to date remained economically viable due only to governmental subsidies.

OBJECTS AND SUMMARY OF THE INVENTION

Therefore, one object of this invention is to provide an improved ethanol production process that results in value added flavor enhancing, nutritional, nutraceutical, and/or pharmaceutical byproducts.

Another object of this invention is to provide an improved ethanol production process that minimizes the amount of VOC and other pollutants released to the atmosphere during the treatment of the whole stillage.

Still another object of this invention is to provide an improved ethanol production process requiring reduced capital equipment investment and reduced maintenance costs.

Other objects and advantages of this invention shall become apparent from the ensuing descriptions of the invention.

Accordingly, an improved ethanol producing process is disclosed wherein a starch-containing feedstock is hydrolyzed to produce ethanol and a whole stillage. The whole stillage comprises the remaining solids, nutrients, yeast and water remaining after the ethanol has been removed during the hydrolysis step. The whole stillage is centrifuged, filtered or otherwise separated by other known techniques to produce wet distillers grain and a thin stillage stream. The wet distillers grain, also known as thick stillage, includes most of the protein containing solids and some of the water comprising the whole stillage. The thin stillage will comprise the nutrients, yeast and most of the water in the whole stillage. The wet distillers grain is dried under conditions that do not denature the proteins contained in the thick stillage, and more preferably, under conditions that minimize the volutizing of the VOC contained in the wet distillers grain. The drying conditions depend on a variety of factors. When utilizing a spray dryer, these factors include the ease in which the wet distillers grain can be atomized, the humidity of the air in the drying environment, the temperature of the hot air used to dry the wet distillers grain, the temperature of the wet distillers grain when it enters the spray drier, and the contact time between the hot air and the atomized wet distillers grain. In a preferred embodiment these factors are controlled to produce a protein rich product having a water content of less than about 15% by weight. It has been found that setting the temperature and contact time to achieve a hot air exhaust temperature between about 140° F. and about 170° F. will result in a protein rich product containing less than about 15% water by weight and whose proteins have not been denatured. Under normal humidity conditions and using a conventional spray dryer an exhaust temperature in the above range should result in an inlet hot air temperature of less than about 450° F., and a contact time of less than about three minutes. Utilization of the above drying conditions will also reduce the VOC emission to the atmosphere. In a preferred embodiment the drying conditions are set to maintain the temperature of the wet distillers grain below the temperature required to volatize most of the VOC's. It is further preferred that any VOC that is volatized pass through a cold trap and then filtered to remove water to produce a VOC product. The VOC product can then be utilized as a supplement to flavor enhance other products.

If desired the thin stillage stream can be sent to an evaporator to remove most of the water to produce the syrup. The syrup can be added to the wet distillers grain prior to the drying step and be processed under the same conditions as the wet distillers grain as described above.

In another alternate embodiment the thin stillage stream is passed through a microfiltration unit utilizing a filter size to form a carotenoid containing retentate and a nutrient rich permeate. A filter having a pore size of about 0.1 to 1.0 micron can be used. The carotenoid containing retentate is then dried to produce a carotenoid rich product having less than about 15% water by weight. It has been found that setting the temperature and contact time to achieve a hot air exhaust temperature between about 140° F. and about 170° F. will result in a carotenoid rich product containing less than about 15% water by weight. Under normal humidity conditions and using a conventional spray dryer an exhaust temperature in the above range should result in an inlet hot air temperature of less than about 450° F., and a contact time of less than about three minutes. In a preferred embodiment any volatized VOC is passed through a cold trap and filter to produce a liquefied VOC product.

In another alternate embodiment the nutrient rich permeate is passed through an ultrafiltration unit utilizing a filter size to form a protein and yeast containing retentate and vitamin and mineral containing permeate. A filter having a pore size of less than about 0.1 microns is preferred. The protein and yeast containing retentate is dried to produce a protein and yeast rich product having less than 15% water by weight. It has been found that setting the temperature and contact time to achieve a hot air exhaust temperature between about 140° F. and about 170° F. will result in a protein and yeast rich product containing less than about 15% water by weight and whose proteins have not been denatured. Under normal humidity conditions and using a conventional spray dryer an exhaust temperature in the above range should result in an inlet hot air temperature of less than about 450° F., and a contact time of less than about three minutes. The vitamin and mineral containing permeate can also be dried under the same conditions as the protein and yeast containing retentate to produce a vitamin and mineral rich product having less than 15% water by weight. It is preferred that any volatized VOC's be passed to a cold trap and filter to produce a liquid VOC product.

BRIEF DESCRIPTION OF THE DRAWINGS

The accompanying drawings illustrate a preferred embodiment of this invention. However, it is to be understood that this embodiment is not intended to be exhaustive, nor limiting of the invention. They are but examples of some of the forms in which the invention may be practiced.

PREFERRED EMBODIMENTS OF THE INVENTION

Without any intent to limit the scope of this invention, reference is made to the figures in describing the preferred embodiments of the invention utilizing corn as the starch containing feedstock. The process described herein can also be used with other starch containing feedstocks such as bagasse, sugar cane, grains, and other starch containing materials.

Figure 1:
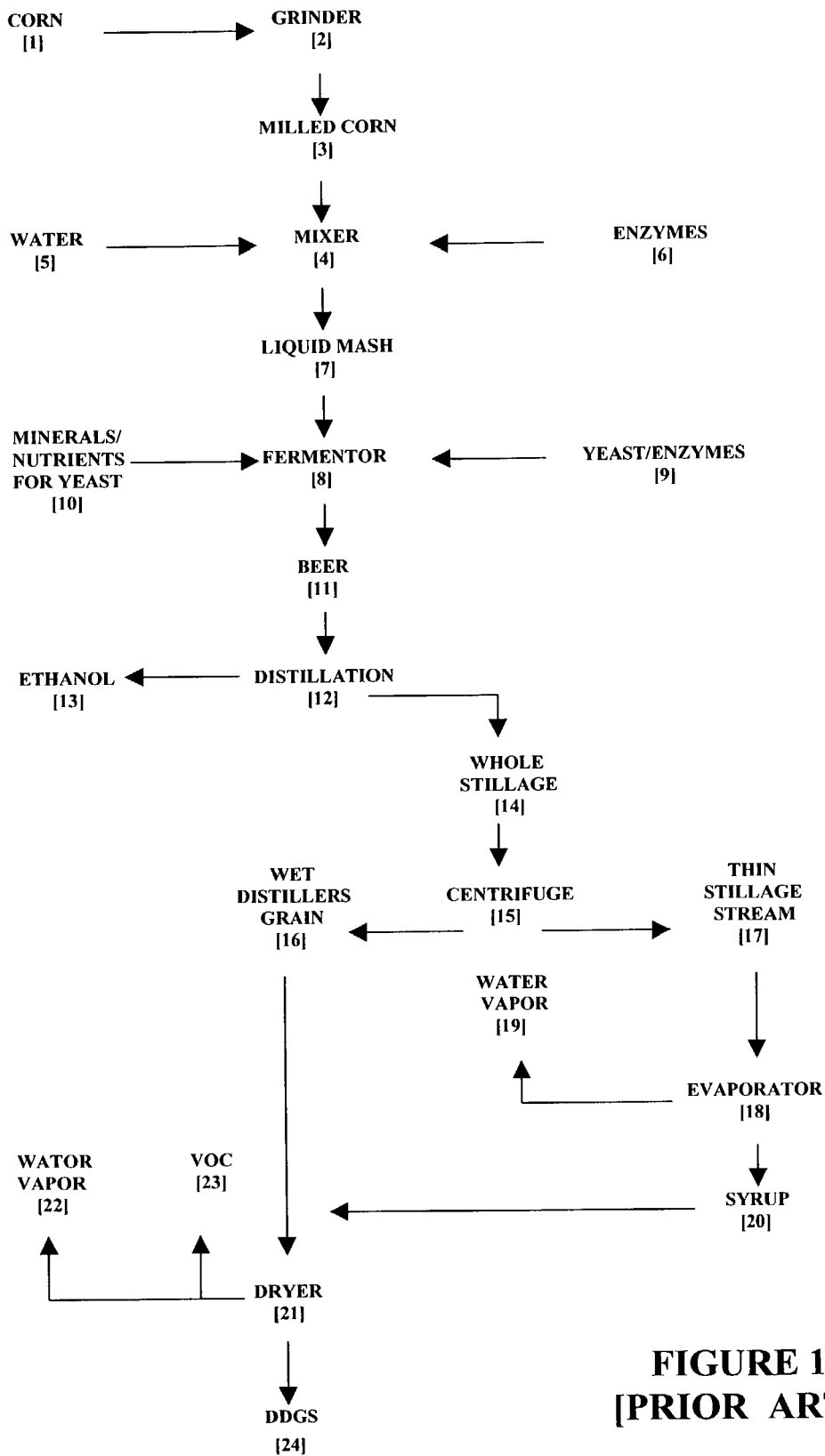
FIG. 1 is a schematic illustrating a conventional prior art ethanol production process.

In a conventional ethanol production process as illustrated in FIG. 1, a starch-containing feedstock 1, such as corn, is fed to a grinder 2 to produce a milled corn 3. The milled corn 3 is then send to a mixer 4 where water 5, as well as enzymes 6, are added to produce a liquid mash 7. The liquid mash 7 is then sent to a fermentation vessel 8 where the desired yeast and additional enzymes 9, as well as the minerals and nutrients 10 necessary for efficient fermentation, are added. After the desired amount of fermentation has been completed the resulting product 11 commonly referred to as the "beer" is sent to a distillation unit 12 where an ethanol rich (about 95% ethanol by weight) stream 13 is separated from the remaining fermented solids and water. The remaining fermented solids and water is generally known as the whole stillage 14. The whole stillage 14 is treated to produce an animal feed commonly known as DDGS. The most common method to treat the whole stillage 14 is to separate the whole stillage 14 by centrifuge 15 to form two separate streams. The first is known as the wet distillers grain 16. The wet distillers grain 16 includes most of the solids and some of the water found in the whole stillage 14. The second stream is known as the thin stillage stream 17. It includes the minerals, nutrients, yeast and the remaining water that was found in the whole stillage 14. In a typical process the thin stillage stream 17 is sent to evaporator 18 where water 19 is removed and the remaining solids or syrup 20 are combined with the wet distillers grain 16 and sent to a drum dryer 21. The dryer 21 is typically operated with the hot air having an inlet temperature at about 1000° F.-1200° F. The hot air will remain in contact with the wet distillers grain 16 and syrup 20 for approximately five minutes before exiting the dryer having an exhaust temperature at about 200° F.-225° F. At these conditions the protein contained in the dried solids 24 are denatured and are only good for use in animal feed known as DDSG. In addition any water vapor 22 and VOC 23 in the wet distillers grain 16 and syrup 20 is volatized and either released to the atmosphere or passed through expensive conventional thermal oxidizers (not shown).

Figure 2:
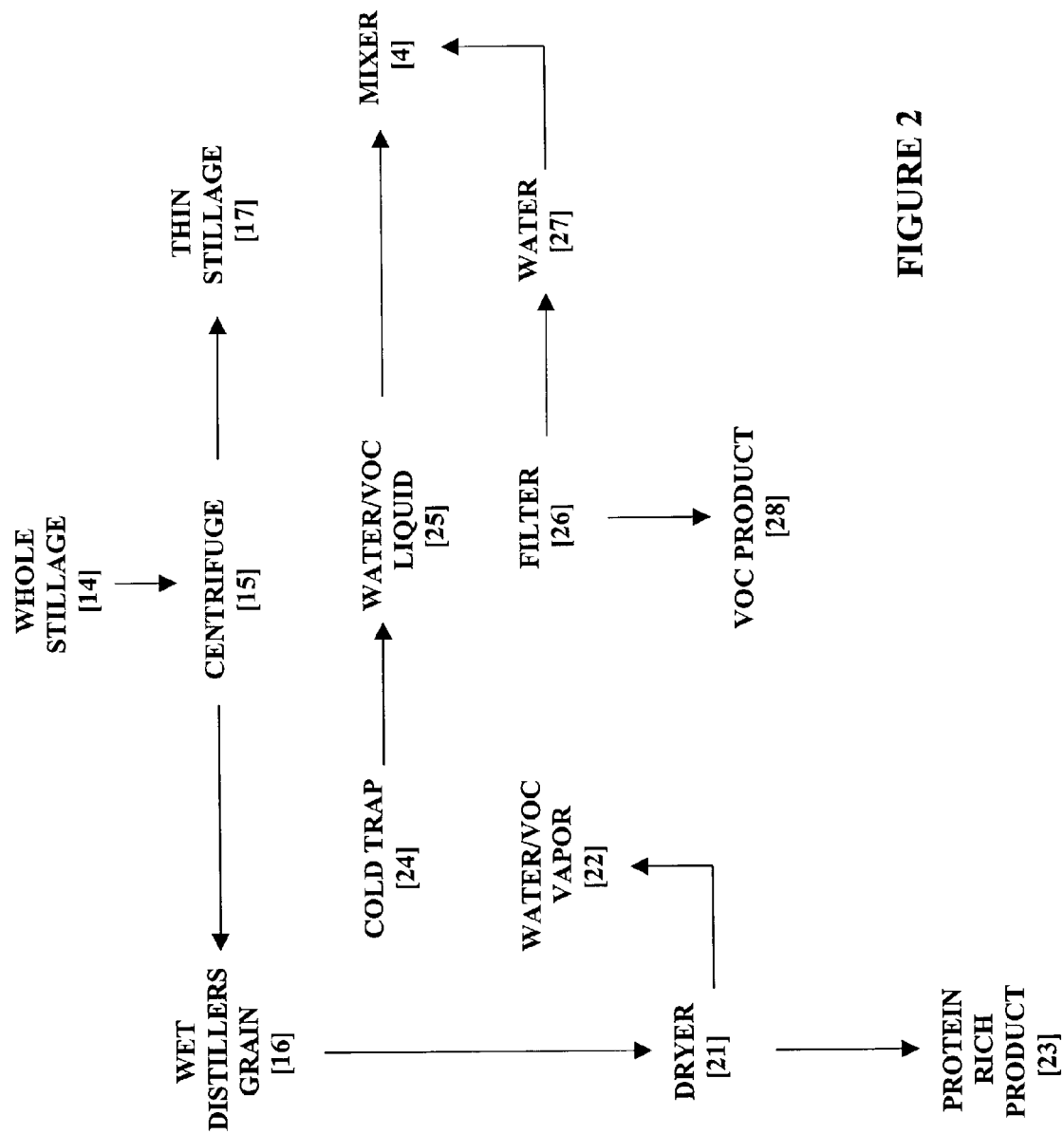
FIG. 2 is a schematic illustrating a preferred embodiment of this invention to treat the wet distillers grain to produce a non-denatured protein rich product.

The process of this invention involves improved treatment of the whole stillage 14 to produce products each having greater economic value than DDGS, as well as significantly reduce the costs of treatment of the emissions from the process. In particular the amount of VOC emissions can be reduced while at the same time producing a flavor enhancement supplement product. Turning now to FIG. 2, the whole stillage 14 is again separated into two product streams by centrifuge 15. Other known separating equipment such as filters could be used. These two streams include the wet distillers grain 16 containing most of the protein compounds found in the whole stillage 14 and the thin stillage stream 15 containing most of the carotenoid, yeast, vitamin, mineral, and remaining protein compounds.

The wet distillers grain 16 is sent to spray dryer 21 that is operated at conditions controlled to produce a protein rich product having a water content of less than about 15% by weight. It has been found that setting the temperatures of the hot air and the wet distiller grain 16, as well as their contact time to achieve a hot air exhaust temperature of between about 140° F. and about 170° F. will result in the production of a protein rich product 23 having a water content of less than about 15% by weight. Under normal humidity conditions a hot air exhaust temperature in the above range would likely require an inlet hot air temperature of less than about 450° F., and a contact time of less than about three minutes. Within these drying conditions the wet distillers grain temperature should remain below the temperature to volatize most, if not all, of the VOC contained in the wet distillers grain. Thus, a significant portion of the VOC will remain in the protein rich product 23. This has the result of not only reducing the VOC that are volutized, but maintaining more of the flavor enhancing compounds in the protein rich product 23. It is also preferred that the protein rich product 23 be cooled upon leaving dryer 21 to prevent any further volutization of the VOC that is contained in the protein rich product 23. One method of cooling the protein rich product 23 is through the use of a fluidized bed wherein cool or ambient temperature air is used to fluidize the bed. Other known cooling techniques could be employed.

The water and any VOC vapor 22 removed during drying can be recycled to the mixer 4. Depending on the dryer operating conditions some VOC may be volatized. Because the volume of the volutized VOC is substantially less than in a conventional whole stillage treatment process, the water and VOC vapor 22 can be sent through a conventional and less expensive cold trap 24 to produce a liquid VOC product 25. Water 26 in the liquid VOC product 25 can be removed, such as by filter 26 or other known separating equipment, to produce a dry VOC product 28 that can be sold as a flavor enhancing additive.

Figure 3:
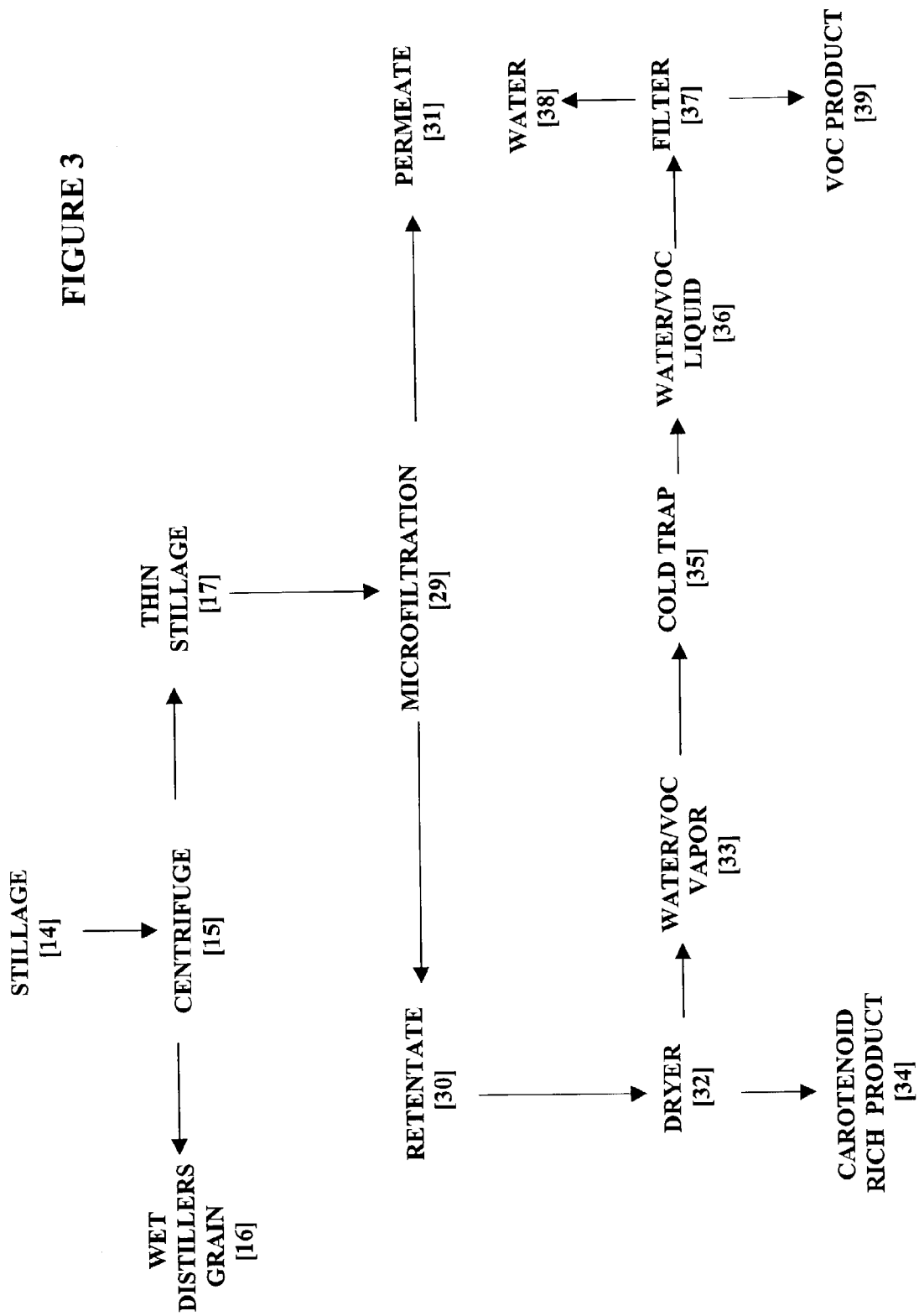
FIG. 3 is a schematic illustrating a preferred embodiment of this invention to treat the thin stillage through use of microfiltration to produce a carotenoid rich product.

Turning now to FIG. 3 in another preferred embodiment the thin stillage 17 is passed through a microfiltration unit 29 having a filter size of about 0.1 to 1.0 micron to form a retentate stream 30 and a permeate stream 31. In a more preferred embodiment the filter size is set to capture in the retentate stream 30 the carotenoid compounds. Carotenoid compounds, particularly Lutien and Zeaxantin, have been found useful in reducing various serious eye diseases such as age related macular degeneration and cataracts. The retentate stream 30 containing the carotenoid compounds is sent to dryer 32. In a preferred embodiment dryer 32 will be operated at a temperature to minimize the denaturing of any protein contained in the retentate stream 30, as well as to prevent volatization of the VOC's in the retentate stream 30 during the period that the retentate stream 30 is contained in the dryer 32. This can be achieved if the retentate stream 30 is retained in dryer 32 for a period of less than about three minutes, and the dryer 32 is operated with a hot air exhaust temperature less than about 170° F. to remove the water. Operated in this manner sufficient water can be removed to form a carotenoid rich product 34 having less than 15% water by weight. Depending on the dryer operating conditions and the retention time of the retentate stream 30 in the dryer 32 some VOC may be volatized. Because the volume of the VOC is substantially less than in a conventional whole stillage treatment process, the water and VOC vapor 33 can be sent through a conventional and less expensive cold trap 35 to produce a liquid VOC stream 36. Stream 36 can be recycled to mixer 4 or preferably the liquid VOC can be separated from the water 38 in stream 36 by a filter 37 to produce VOC product 39 that can be sold as a flavor enhancing additive.

Figure 4:
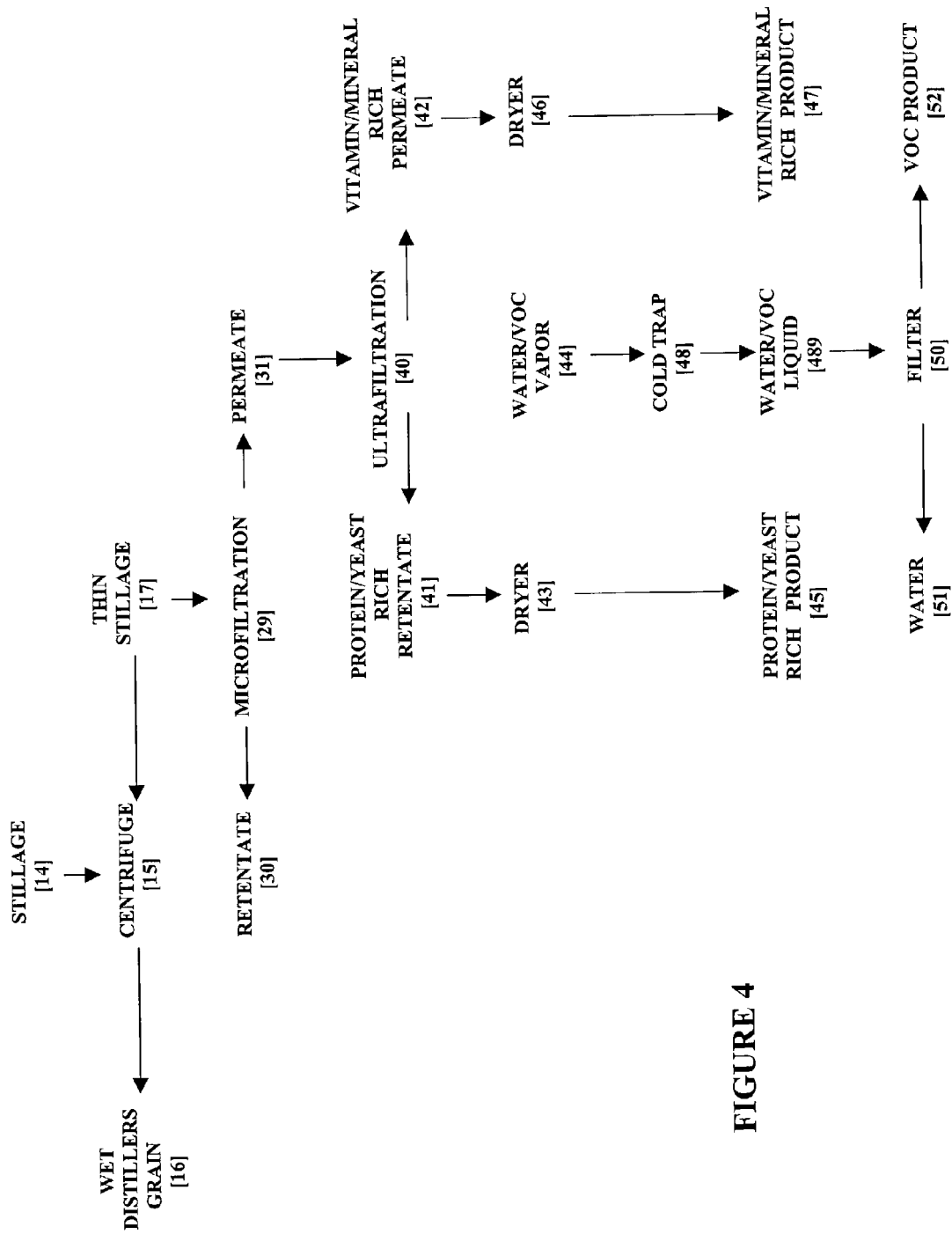
FIG. 4 is a schematic illustrating a preferred embodiment of this invention to treat the permeate stream from the microfiltration through use of ultrafiltration to produce a protein/yeast rich product and/or a vitamin/mineral rich product.

Turning now to FIG. 4 in another preferred embodiment the permeate 31 is passed through an ultrafiltration unit 40. The filter size is selected to be less than about 100,000 molecular weight to produce a protein and yeast rich retentate 41 and a vitamin and mineral rich permeate 42. The protein and yeast rich retentate 41 is sent to dryer 43 to remove at least a substantial portion of the water from the retentate 41. It is preferred that the dryer 43 be operated to minimize the volalization of any VOC's in the retentate 41. This can be achieved by utilizing the same operating conditions as described above for dryer 32. Operated in this manner sufficient water can be removed to form a protein and yeast rich product 45 having less than 15% water by weight. Depending on the dryer operating conditions and the retention time of the protein and yeast retentate 41 in the dryer 43 some VOC may be volatized. Because the volume of the VOC is substantially less than in a conventional whole stillage treatment process, the water and VOC vapor 44 can be sent through a conventional and less expensive cold trap 48 to produce a liquid VOC stream 49. Stream 49 can be recycled to mixer 4 or preferably the water 51 in stream 41 can be separated by filter 50 to form a VOC product 52 that can be sold as a flavor enhancing additive.

In another preferred embodiment the vitamin and mineral rich permeate 42 is sent to the dryer 46 to remove at least a substantial portion of the water in permeate 42. It is preferred that the dryer 46 be operated to minimize the volalization of any VOC's in the permeate 42. This can be achieved by operating dryer 46 under the same conditions as dryer 43. Operated in this manner sufficient water can be removed to form a vitamin and mineral rich byproduct 47 having less than 15% water by weight. Depending on the dryer operating conditions and the retention time of the permeate 42 in the dryer 46 some VOC may be volatized. Because the volume of the VOC is substantially less than in a conventional stillage treatment process, the water and VOC vapor can be sent through a conventional and less expensive cold trap 48 to produce a liquid VOC stream similar to stream 49. This stream can also be recycled to mixer 4 or passed through a filter, such as filter 50, to form a VOC product that can be sold as a flavor enhancing additive.

Thus, as shown in the FIGS. 2-4, the whole stillage 14 can be processed to produce a protein rich product 23, a carotenoid rich product 34, a protein and yeast rich product 45, and a vitamin and mineral rich product 47 with minimum or no VOC's released to the atmosphere. The VOC's produced do not have to be treated by expensive thermal oxidizers or similar equipment, but Can be sent to a less expensive cold trap and filter to produce yet another value added product, Liquid VOC's. Each of these five product streams has significantly greater commerial value than the currently produced animal feed DDGS.

It is not necessary that separate cold traps be used for each of the product streams.

Depending on the amount of VOC volatized, the different VOC streams volatized can be combined and sent to one or more of the cold traps, thus further reducing capital expense. Depending on the product desired it is also possible to direct various streams to a common dryer. There are of course other alternate embodiments that are obvious from the foregoing descriptions of the invention which are intended to be included within the scope of the invention as defined by the following claims.

We claim:

1. An ethanol production process wherein a corn feedstock is hydrolyzed to produce ethanol and whole stillage, the improvement to which comprises:
   a. reducing production of a volatile organic compounds stream by separating the whole stillage to produce a wet distillers grain containing protein-containing solids and a thin stillage containing a solubles stream containing vitamins, minerals, proteins and yeast;
   b. filtering at least a portion of the thin stillage through a microfilter to form a carotenoid-containing retentate and a water soluble permeate comprising vitamin, mineral, protein and yeast; and
   c. filtering at least a portion of the water soluble permeate through an ultrafilter to produce a protein and yeast-containing retentate and a vitamin and mineral-containing permeate;
   d. drying at least one from the group consisting of: wet distillers grain, the carotenoid-containing retentate, the protein and yeast containing retentate and the vitamin and mineral-containing permeate in a spray dryer operating at an inlet hot air temperature of less than about 450° F. and an exhaust temperature of between about 140° F. and about 170° F. for a period of time to produce at least one product having a water content of less than about 15% by weight and a reduced stream of volatile organic compounds.

2. The ethanol production process according to claim 1 further comprising drying the water-soluble permeate under operating conditions to produce a vitamin, mineral, protein and yeast-rich product having a water content of less than about 15% by weight.

3. The process according to claim 1 wherein filtering the at least a portion of the water soluble permeate comprises an ultrafilter having a pore size of less than about 100,000 molecular weight and drying the protein and yeast-containing retentate.

4. The process according to claim 1 wherein the wet distillers grain, the retentate, the protein and yeast containing retentate, and the vitamin and mineral-containing permeate are each dried separately to produce four products.

5. The process according to claim 1 wherein said drying produces at least one vapor stream comprising volatile organic compounds.

6. The process according to claim 1 wherein said volatile organic compounds are retained by a cold trap.

7. An ethanol production process wherein a starch-containing feedstock is hydrolyzed to produce ethanol and whole stillage, the improvement to which consists essentially of:
   a. reduction of capital expense and production of a volatile organic compound stream by separating the whole stillage to produce a wet distillers grain containing a protein-containing solids stream and a thin stillage containing a solubles stream containing vitamins, minerals, proteins and yeast;
   b. filtering the thin stillage solubles stream through a microfilter having a pore size of about 0.1-1.0 microns to form a carotenoid-containing retentate and a permeate stream;
   c. filtering the permeate stream through an ultrafilter having a filter size of less than about 100,000 molecular weight to obtain a protein and yeast-containing retentate and a vitamin and mineral containing permeate; and
   d. employing conditions for drying said wet distillers grain, said carotenoid-containing retentate, said protein and yeast-containing retentate and said vitamin and mineral containing permeate to a water content of less than about 15% by weight including operating a spray dryer to achieve hot air exhaust temperature between about 140° F. and about 170° F. for a period of time equal to about three minutes but not more than three minutes.

8. The ethanol production process according to claim 7 further comprising drying said wet distillers grain to produce a first water-containing vapor stream and drying said protein and yeast-containing retentate to produce a second water-containing vapor stream.

9. The ethanol production process according to claim 8 wherein drying said carotenoid containing retentate produces a third water-containing vapor stream.

10. An improvement to an ethanol production process wherein a starch-containing feedstock is hydrolyzed to produce ethanol and whole stillage, the whole stillage including protein containing solids, the improvement to which consists essentially of:
   a. separating the whole stillage to produce a wet distillers grain comprising most of the protein containing solids and a thin stillage comprising vitamins, minerals, proteins and yeast;
   b. filtering the thin stillage solubles to form a first retentate and a first permeate;
   c. filtering the first permeate stream to obtain a second retentate and a second permeate; and
   d. selecting at least one from the group consisting of the first retentate, the second retentate, the second permeate, and wet distillers grain and drying to a water content of less than about 15% by weight by operating a spray dryer at an inlet temperature of less than about 450° F. and an outlet temperature between about 140° F. and about 170° F. for a period of time adequate to produce at least one product comprising non-denatured proteins and a reduced stream of volatile organic compounds.

* * * * *